United States Patent
Mallaby

(10) Patent No.: US 9,510,854 B2
(45) Date of Patent: Dec. 6, 2016

(54) THROMBECTOMY CATHETER WITH CONTROL BOX HAVING PRESSURE/VACUUM VALVE FOR SYNCHRONOUS ASPIRATION AND FLUID IRRIGATION

(75) Inventor: Mark Mallaby, San Diego, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1241 days.

(21) Appl. No.: 12/250,286

(22) Filed: Oct. 13, 2008

(65) Prior Publication Data

US 2010/0094201 A1  Apr. 15, 2010

(51) Int. Cl.
  *A61B 17/3203* (2006.01)
  *A61B 17/22* (2006.01)

(52) U.S. Cl.
  CPC .......... *A61B 17/32037* (2013.01); *A61B 2017/22079* (2013.01); *A61B 2217/005* (2013.01); *A61B 2217/007* (2013.01)

(58) Field of Classification Search
  CPC .......... A61B 17/320068; A61B 2017/22079; A61B 2217/005; A61B 2217/007; A61M 1/0064; A61M 1/0084; A61F 9/00745
  USPC .......... 604/22, 31, 65, 67, 70, 118–120, 525; 606/159
  See application file for complete search history.

(56) References Cited

U.S. PATENT DOCUMENTS

| | | | |
|---|---|---|---|
| 3,589,363 A * | 6/1971 | Banko | A61B 17/320068 604/22 |
| 3,693,613 A | 9/1972 | Kelman | |
| 3,818,913 A * | 6/1974 | Wallach | A61F 9/00736 604/28 |
| 3,930,505 A * | 1/1976 | Wallach | A61M 1/0084 604/22 |
| 4,274,411 A * | 6/1981 | Dotson, Jr. | A61F 9/00763 128/910 |
| 4,299,221 A * | 11/1981 | Phillips | A61C 17/04 433/100 |
| 4,465,470 A * | 8/1984 | Kelman | 604/27 |
| 4,690,672 A | 9/1987 | Veltrup | |
| 4,832,685 A * | 5/1989 | Haines | A61F 9/00745 604/30 |
| 5,135,482 A | 8/1992 | Neracher | |
| 5,318,518 A | 6/1994 | Plechinger et al. | |
| 5,322,504 A | 6/1994 | Doherty et al. | |
| 5,342,293 A | 8/1994 | Zanger | |
| 5,395,315 A | 3/1995 | Griep | |
| 5,403,276 A * | 4/1995 | Schechter | A61B 17/32002 604/118 |

(Continued)

FOREIGN PATENT DOCUMENTS

DE 37 15 418 A1 11/1987
EP 806213 A1 * 11/1997 .............. A61M 1/00

(Continued)

*Primary Examiner* — Kami A Bosworth
*Assistant Examiner* — Matthew A Engel
(74) *Attorney, Agent, or Firm* — Seager Tufte & Wickhem LLP

(57) ABSTRACT

A thrombectomy system comprising an aspiration catheter having an aspiration lumen and a high pressure irrigation lumen, the aspiration catheter having a proximal end and a distal, and a control box fluidly connected to the aspiration catheter and configured to synchronously provide irrigation and vacuum through the aspiration catheter.

23 Claims, 3 Drawing Sheets

(56) References Cited

U.S. PATENT DOCUMENTS

| | | | |
|---|---|---|---|
| 5,496,267 A * | 3/1996 | Drasler | A61B 17/32037 604/22 |
| 5,536,242 A | 7/1996 | Willard et al. | |
| 5,624,394 A * | 4/1997 | Barnitz et al. | 604/67 |
| 5,669,876 A * | 9/1997 | Schechter | A61B 17/32002 128/898 |
| 5,713,851 A | 2/1998 | Boudewijn et al. | |
| 5,730,717 A | 3/1998 | Gelbfish | |
| 5,795,322 A | 8/1998 | Boudewijn | |
| 5,827,229 A | 10/1998 | Auth et al. | |
| 5,843,022 A | 12/1998 | Willard et al. | |
| 5,853,384 A * | 12/1998 | Bair | A61B 17/3203 604/141 |
| 5,916,192 A | 6/1999 | Nita et al. | |
| 5,989,210 A | 11/1999 | Morris et al. | |
| 6,096,001 A | 8/2000 | Drasler et al. | |
| 6,129,697 A | 10/2000 | Drasler et al. | |
| 6,129,698 A | 10/2000 | Beck | |
| 6,196,989 B1 * | 3/2001 | Padget et al. | 604/27 |
| 6,224,570 B1 | 5/2001 | Le et al. | |
| 6,375,635 B1 * | 4/2002 | Moutafis | A61B 17/3203 604/22 |
| 6,544,209 B1 | 4/2003 | Drasler et al. | |
| 6,572,578 B1 | 6/2003 | Blanchard | |
| 6,599,271 B1 * | 7/2003 | Easley | 604/119 |
| 6,616,679 B1 | 9/2003 | Khosravi et al. | |
| 6,635,034 B1 * | 10/2003 | Cosmescu | A61B 18/14 601/35 |
| 6,635,070 B2 | 10/2003 | Leeflang et al. | |
| 6,719,717 B1 | 4/2004 | Johnson et al. | |
| 6,755,803 B1 * | 6/2004 | Le et al. | 604/22 |
| 6,926,726 B2 | 8/2005 | Drasler et al. | |
| 8,945,030 B2 * | 2/2015 | Weston | A61M 1/0088 602/2 |
| 2002/0068895 A1 | 6/2002 | Beck | |
| 2002/0173819 A1 | 11/2002 | Leeflang et al. | |
| 2003/0144688 A1 | 7/2003 | Brady et al. | |
| 2004/0193046 A1 | 9/2004 | Nash et al. | |
| 2004/0199201 A1 | 10/2004 | Kellett et al. | |
| 2004/0243157 A1 | 12/2004 | Connor et al. | |
| 2005/0240146 A1 * | 10/2005 | Nash et al. | 604/35 |
| 2006/0064123 A1 * | 3/2006 | Bonnette et al. | 606/167 |
| 2006/0229550 A1 * | 10/2006 | Staid | A61B 17/3203 604/27 |
| 2008/0097563 A1 | 4/2008 | Petrie et al. | |
| 2008/0125698 A1 * | 5/2008 | Gerg | A61F 9/00736 604/35 |
| 2009/0048607 A1 * | 2/2009 | Rockley | A61F 9/00745 606/107 |
| 2009/0306476 A1 * | 12/2009 | Banik | A61B 1/00068 600/158 |
| 2010/0030134 A1 * | 2/2010 | Fitzgerald | A61M 1/0031 604/34 |
| 2010/0094201 A1 * | 4/2010 | Mallaby | A61B 17/32037 604/28 |
| 2010/0145302 A1 * | 6/2010 | Cull | A61M 1/0031 604/505 |
| 2011/0092892 A1 * | 4/2011 | Nitsan | A61B 1/00068 604/28 |
| 2013/0245543 A1 * | 9/2013 | Gerg | A61M 1/0058 604/30 |

FOREIGN PATENT DOCUMENTS

| | | |
|---|---|---|
| EP | 1 488 748 | 12/2004 |
| WO | 96/01079 A1 | 1/1996 |
| WO | 2004/100772 | 11/2004 |
| WO | 2008/097993 A2 | 8/2008 |

* cited by examiner

THROMBECTOMY CATHETER WITH CONTROL BOX HAVING PRESSURE/VACUUM VALVE FOR SYNCHRONOUS ASPIRATION AND FLUID IRRIGATION

TECHNICAL FIELD

The present disclosure pertains generally to medical devices and methods of their use. More particularly, the present invention pertains to aspiration and thrombectomy devices and methods of use thereof.

BACKGROUND

Several devices and systems already exist to aid in the removal of thrombetic material. These include simple aspiration tube type devices using vacuum syringes to extract thrombus into the syringe, simple flush-and-aspirate devices, more complex devices with rotating components the pull in, macerate and transport thrombetic material away from the distal tip using a mechanical auger, systems that use very high pressure to macerate the thrombus and create a venturi effect to flush the macerated material away.

All of the devices described above have limitations as a result of individual design characteristics. For example, simple aspiration catheters off ease of use and rapid deployment but may become blocked or otherwise inoperable when faced with older, more organized thrombetic material. Such devices must be removed and cleared outside the body and then re-inserted into the vasculature, which lengthens the time needed for the procedure and increases the opportunity to kink the catheter shaft. Such kinks may reduce performance by decreasing the cross-sectional area of the catheter or may render the device inoperable. The use of a syringe to provide vacuum, moreover, may increase the risk of operator error by not preventing the operator from applying positive pressure to the aspiration lumen and thereby expelling loose embolic material into the patient vasculature.

Mechanical rotary devices use an auger to grab and carry the thrombus away from the target area. Some create transport force via vacuum bottles while others create differential pressure at the distal tip of the device with the auger acting as a low pressure pump. These devices typically work slowly and offer the physician no feedback as to when the device should be advanced further into the lesion.

Flushing type devices include manual flush type devices in which the physician manipulates a hand-driven pump to provide flowing saline at the tip of the device to break up and aspirate the thrombus material, which may introduce performance variations based on the ability of the physician to consistently pump the device over the duration of the procedure. Flushing devices also include high pressure flushing devices that macerate the thrombus and then, using a vortex created by the high pressure fluid, transport the emulsified thrombetic material to a collection bag. These devices are effective at removing all levels of thrombetic material, but the pressure created by the device is so great that its action against certain vessel walls may interrupt the heart muscle stimulation mechanism and creates a bradycardia event in certain patients that requires a pacing lead to be placed in the patient prior to use. Further, interacting with the thrombetic material outside of the catheter may allow loose material to escape the capture mechanism.

Thus, a need remains for improved thrombus removal capability particularly for systems that have increased reliability, are more benign and offer greater feedback capabilities.

SUMMARY

The disclosure pertains generally to devices such as an assisted aspiration catheter for removing a range of thrombetic material from the general vascular system, natural or synthetic tubule or cavity found in the human body of a patient via standard vascular access using the Seldinger technique.

In one illustrative but non-limiting example, a vacuum source is connected to the proximal end of a flexible, kink resistant tube or aspiration lumen or catheter. The other end of the aspiration lumen is open to patient vasculature to allow thrombetic material to be drawn into the aspiration lumen via the suction provided by the vacuum source. The vacuum source may also act as a containment vessel for aspirated thrombetic material. A second flexible tube that may be housed inside the aspiration lumen conveys a pressurized stream of sterile saline or other physiologic solution to a specifically placed orifice near the distal end of the aspiration lumen. A control system may be provided that ensures the synchronous operation of the vacuum source and the pressurized stream. Thereby thrombetic material may be drawn by vacuum into the distal opening of the catheter. Less organized thrombetic material may be immediately aspirated into the containment vessel and more organized thrombetic material may be removed by being drawn into the catheter and is macerated by a high-pressure fluid stream within the catheter opening and aspirated into the containment vessel.

The above summer summary of some embodiments is not intended to describe each disclosed embodiment or every implementation of the present invention. The Figures and Detailed Description that follow more particularly exemplify these embodiments.

Figure 1:
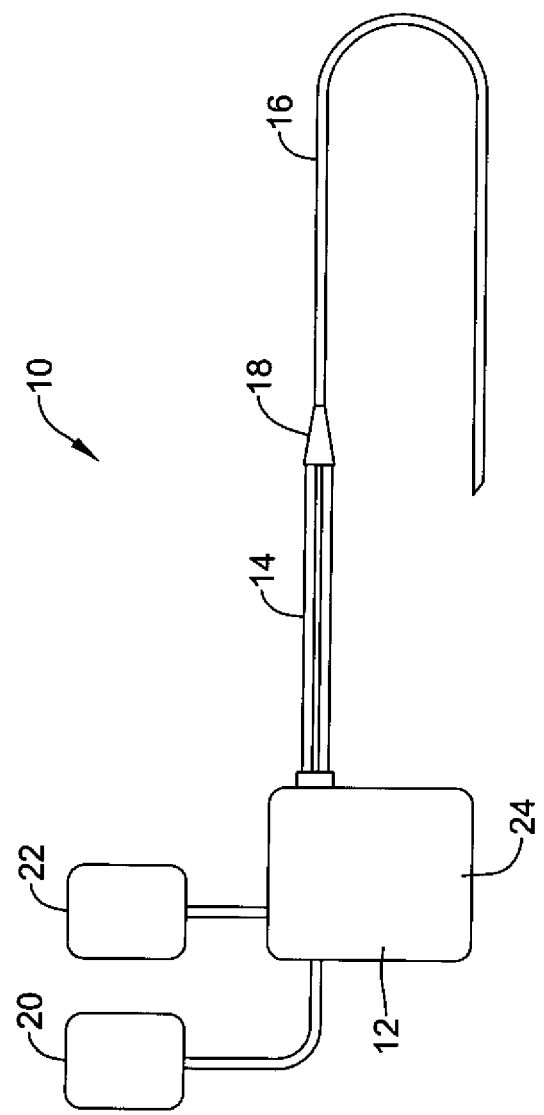
FIG. 1 is a diagrammatic view of as assisted aspiration catheter system 10.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the claims.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a diagrammatic figure depicting assisted aspiration system 10. Aspiration system 10 includes a remote hand piece 12 that contains the fluid pump and the operator control interface. In one contemplated embodiment, system 10 is a single use disposable unit. Aspiration system 10 may also include extension tubing 14, which contains lumens both for fluid irrigation and for aspiration, and which allows independent manipulation of a catheter 16 without requiring repositioning of hand piece 12 during the procedure. Extension tubing 14 may also act as a pressure accumulator. High pressure fluid flow from the displacement pump pulses with each stroke of the pump creating a sinusoidal pressure map with distinct variations between the peaks and valleys of each sine wave. Extension tubing 14 may be matched to the pump to expand and contract in unison with each pump pulse to reduce the variation in pressure caused by the pump pulses to produce a smooth or smoother fluid flow at tip of catheter 16. Any tubing having suitable compliancy characteristics may be used. The extension tubing may be permanently attached to the pump or it may be attached to the pump by a connector. The connector is preferably configured to ensure that the extension tubing cannot be attached to the pump incorrectly.

An interface connector 18 joins extension tubing 14 and catheter 16 together. In one contemplated embodiment, interface connector 18 may contain a filter assembly (not shown) between high pressure extension tubing 14 and the high pressure irrigation lumen of catheter 16. The catheter and extension tube may be permanently joined by connector 18. Alternatively, interface connector 18 may contain a standardized connection so that a selected catheter 16 may be attached to extension tubing 14.

Attached to hand piece 12 are a fluid source 20 and a vacuum source 22. A standard hospital saline bag may be used as fluid source 20; such bags are readily available to the physician and provide the necessary volume to perform the procedure. Vacuum bottles may provide the vacuum source 22 or the vacuum source may be provided by a syringe, a vacuum pump or other suitable vacuum source.

In one contemplated embodiment, catheter 16 has a variable stiffness ranging from stiffer at the proximal end to more flexible at the distal end. The variation in the stiffness of catheter 16 may be achieved with a single tube with no radial bonds between two adjacent tubing pieces. For example, the shaft of catheter 16 may be made from a single length of metal tube that has a spiral cut down the length of the tube to provide shaft flexibility. Variable stiffness may be created by varying the pitch of the spiral cut through different lengths of the metal tube. For example, the pitch of the spiral cut may be greater (where the turns of the spiral cut are closer together) at the distal end of the device to provide greater flexibility. Conversely, the pitch of the spiral cut at the proximal end may be lower (where the turns of the spiral cut are further apart) to provide increased stiffness. A single jacket covers the length of the metal tube to provide for a vacuum tight catheter shaft. Other features of catheter 16 are described with reference to FIG. 3, below.

Figure 2:
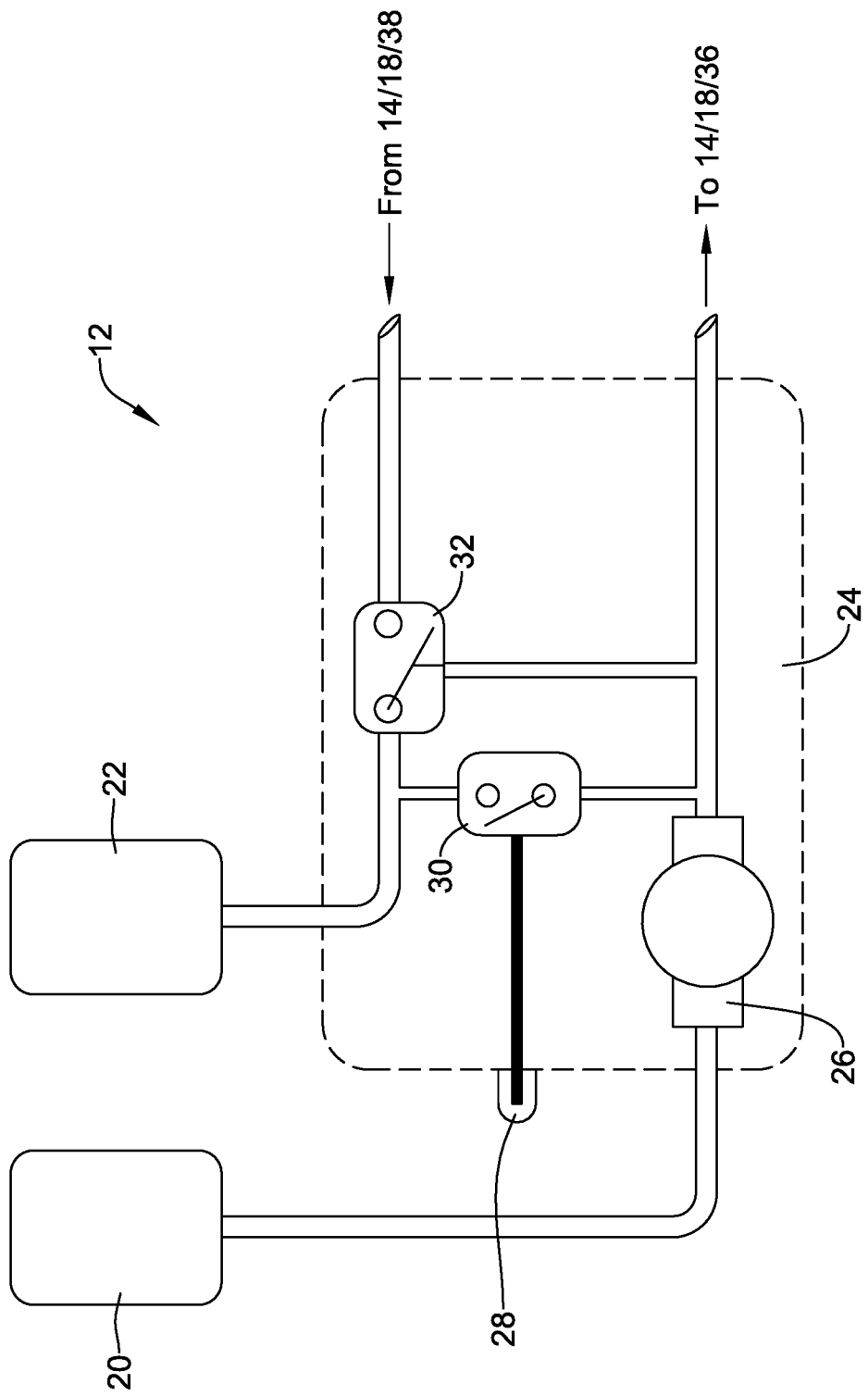
FIG. 2 is a diagrammatic view showing more detail of the proximal portion of assisted catheter aspiration system 10.

FIG. 2 is a diagrammatic view showing more detail of hand piece 12 and the proximal portion of assisted catheter aspiration system 10. Hand piece 12 includes a control box 24 where the power and control systems are disposed. A pump 26 may be motor driven displacement pump that has a constant output of less than 30% of the total aspiration volume, based on the minimum catheter dimensions. This pump displacement to catheter volume ensures that no energy is transferred to the patient from the saline pump as all pressurized fluid is evacuated by the aspiration lumen. A prime button 28 is mechanically connected to a prime valve 30. When preparing the device for use, it is advantageous to evacuate all air from the pressurized fluid system to reduce the possibility of air embolization. By depressing prime button 28, the user connects fluid source 20 to vacuum source 22 via the pump 26. This forcefully pulls fluid through the entire pump system, removing all air and positively primes the system for safe operation. A pressure/vacuum valve 32 is used to turn the vacuum on and off synchronously with the fluid pressure system. One contemplated valve 32 is a ported one way valve. Such a valve is advantageous with respect to manual or electronic valve systems because it acts as a tamper proof safety feature by mechanically and automatically combining the operations of the two primary systems. By having pressure/vacuum valve 32, the possibility of turning the vacuum on without activating the fluid system is eliminated.

An electronic control board (not shown) is used to provide the operator interface by use of switches and indicator lamps. The control board also monitors and controls several device safety functions, which include over pressure and air bubble detection and vacuum charge. In one contemplated embodiment, the pump pressure is proportional to the electric current needed to produce that pressure. Consequently, if the electric current required by pump 26 exceeds a preset limit, the control board will disable the pump by cutting power to it. Air bubble detection may also be monitored by electrical current going to the pump. In order for a displacement pump to reach high fluid pressures, there should be little or no air (which is highly compressible) present in the pump or connecting system. The fluid volume is small enough that any air in the system will result in no pressure being generated at the pump head. The control board monitors the pump current for any abrupt downward change that may indicate that air has entered the system. If the rate of drop is faster than a preset limit, the control board will disable the pump by cutting power to it until the problem is corrected. The vacuum line may be connected to a negative pressure sensor. If the vacuum is vacuum source 22 is low or if a leak is detected in the vacuum system, the control board disables the pump until the problem is corrected. The vacuum sensor may also be part of the safety circuit that will not allow the pump to run if vacuum is not present. Thereby a comprehensive safety system that requires both pump pressure and vacuum pressure for the system to run. If a problem exists, the control board will not allow the user to operate the device until all problems are corrected.

Figure 3:
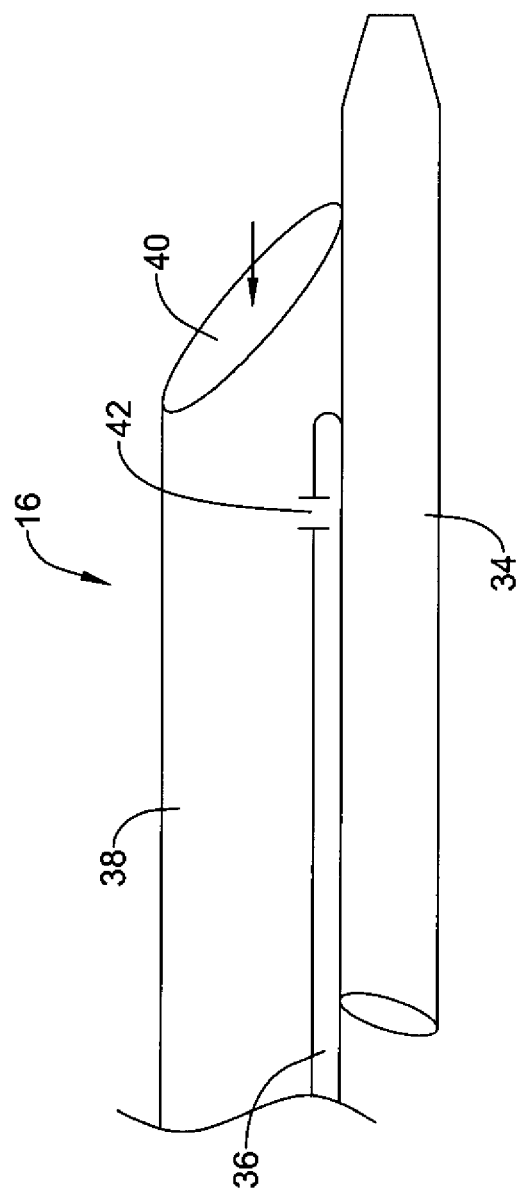
FIG. 3 is a diagrammatic view of the distal end portion of assisted catheter aspiration system 10.

FIG. 3 is a diagrammatic view of the distal end portion of assisted catheter aspiration system 10, showing more details of catheter 16. Catheter 16 is a single-operator exchange catheter and includes a short guidewire lumen 34 attached to the distal end of the device. Guidewire lumen can be between 1 and 30 cm in length, more preferable between 5 and 25 cm in length, or between 5 and 20 cm in length, or approximately 15 cm in length. Aspiration lumen 38 includes a distal opening 40 to allow the vacuum to draw thrombetic material into the lumen. A high pressure irrigation lumen 36 includes a distal orifice 42 that is set proximally of distal opening 40 by a set amount. For example, distal orifice 42 can be set proximally of distal opening 40 by about 0.020", more preferably by 0.020"+−0.003" or by another desired amount. Orifice 42 is configured to spray across the aspiration lumen to dilute the thrombetic material for transport to vacuum source 22. The axial placement of the fluid orifice 42 is such that the spray pattern interaction with the opposing lumen wall preferably produces a spray mist and not a swirl pattern that could force embolic material out from the distal opening 40. The irrigation fluid preferably leaves orifice 42 at between 200 and 450 psi and more preferably at between 250 and 300 psi.

Other contemplated catheters are disclosed in co-pending application Ser. No. 12/026,317 to Jensen et al., entitled "Thrombectomy Apparatus and Method" and filed Feb. 5, 2008, which is incorporated by reference.

In some cases, parts or all of the devices described herein may be doped with, made of, coated with, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like.

In some instances, a degree of MRI compatibility may be imparted into parts of the devices described herein. For example, to enhance compatibility with Magnetic Resonance Imaging (MRI) machines, it may be desirable to make various portions of the devices described herein from materials that do not substantially distort MRI images or cause substantial artifacts (gaps in the images). Some ferromagnetic materials, for example, may not be suitable as they may create artifacts in an MRI image. In some cases, the devices described herein may include materials that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some instances, some of the devices described herein may include a coating such as a lubricious coating or a hydrophilic coating. Hydrophobic coatings such as fluoropolymers provide a dry lubricity. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

It should be understood that this disclosure is, in many respects, only illustrative. Changes may be made in details, particularly in matters of shape, size, and arrangement of steps without exceeding the scope of the invention. The scope of the invention is, of course, defined in the language in which the appended claims are expressed.

REFERENCE NUMERAL LIST

10 Assisted Aspiration Catheter System
12 Hand Piece
14 Extension Tubing
16 Catheter
18 Connector
20 Fluid Source
22 Vacuum Source
24 Control Box
26 Pump
28 Prime Button
30 Prime Valve
32 Pressure/Vacuume Valve
34 Guidewire Lumen
36 High Pressure Irrigation Lumen
38 Aspiration Lumen
40 Distal Opening
42 Orifice

I claim:

1. A thrombectomy system, comprising:
an aspiration catheter having an aspiration lumen and a high pressure irrigation lumen, the aspiration catheter having a proximal end and a distal end;
a fluid source;
a vacuum source producing a vacuum; and
a control box fluidly connecting the fluid source and the vacuum source to the high pressure irrigation lumen and the aspiration lumen, respectively;
wherein the control box is configured to provide high pressure irrigation fluid to the high pressure irrigation lumen when the vacuum is present in the aspiration lumen, and to prevent high pressure irrigation fluid from being provided to the irrigation lumen when the vacuum is not present in the aspiration lumen;
wherein the aspiration lumen has a distal opening and wherein the high pressure irrigation lumen has a distal orifice directed into the aspiration lumen and configured to release a jet of irrigation fluid across the width of the aspiration lumen against an opposing wall of the aspiration lumen, wherein the distal orifice is proximal of the distal opening by at least 0.02 cm;
wherein the jet forms a spray pattern that interacts with the opposing wall of the aspiration lumen in such a way that embolic material is diluted for aspiration and not forced out of the distal opening;
wherein the control box includes a pressure/vacuum valve interposed along the aspiration lumen between the vacuum source and the distal opening;
wherein the pressure/vacuum valve turns the vacuum source on and off synchronously with the high pressure irrigation fluid.

2. The system of claim 1, wherein providing irrigation through a first passage in the control box opens a second passage fluidly connected to the aspiration lumen.

3. The system of claim 2 wherein the control box further includes a displacement pump providing irrigation pressure.

4. The system of claim 3 further comprising tubing fluidly connecting the control box to the aspiration and high pressure irrigation lumens.

5. The system of claim 4 wherein operation of the pump produces fluid pressure pulses and wherein the tubing operates to damping the fluid pressure pulses.

6. The system of claim 5 wherein the catheter irrigation lumen has a compliancy along a proximal region thereof and wherein the tubing has a compliancy that is greater than that of the proximal region of the catheter aspiration lumen.

7. The system of claim 5 wherein the tubing comprises a compliant polymeric material.

8. The system of claim 4 further comprising an interface connector disposed between the tubing and the aspiration catheter whereby the aspiration catheter is detachable and reattachable to the tubing.

9. The system of claim 8 wherein the connector fluidly connects the tubing and the high pressure irrigation lumen.

10. The system of claim 4 wherein the control box is permanently attached to the tubing and wherein the tubing is permanently attached to the aspiration catheter.

11. The system of claim 10 further comprising an interface connector disposed between the tubing and the aspiration catheter.

12. The system of claim 3, further comprising a control board, wherein the control board is configured to cut power to the pump when a sensed current at the pump is out of a predetermined range.

13. The system of claim 3, further comprising a control board, wherein the control board is configured to cut power to the pump when a sensed current at the pump drops faster than a preset limit.

14. The system of claim 3, further comprising a control board, wherein the control board is configured to cut power to the pump when a sensed vacuum pressure at the second passage is out of a predetermined range.

15. The system of claim 3, wherein the vacuum source is a vacuum bottle.

16. The system of claim 3, wherein the fluid source is a saline bottle.

17. The system of claim 2 wherein the pressure/vacuum valve is a mechanical valve such that fluid pressure in the first passage operates the valve.

18. The system of claim 2 wherein the pressure/vacuum valve is controlled electronically.

19. The system of claim 2 further comprising a priming valve fluidly connecting the first and second passages when opened.

20. The system of claim 1 wherein the distal orifice is further configured such that the jet of irrigation fluid is released normal to a longitudinal axis of the aspiration lumen.

21. A method of removing a thrombus, comprising the steps of:
 inserting the aspiration catheter of the thrombectomy system of claim 1 percutaneously into a body vessel lumen;
 advancing the aspiration catheter to a region of interest; and
 operating the control box to synchronously provide high pressure irrigation and aspiration through the aspiration catheter to draw the thrombus into the aspiration lumen.

22. The method of claim 21, wherein the system of claim 1 further provides irrigation through a first passage in the control box opening a second passage fluidly connected to the aspiration lumen,
 wherein the pressure/vacuum valve is a mechanical valve such that fluid pressure in the first passage operates the valve.

23. The method of claim 21, wherein the system of claim 1 further provides irrigation through a first passage in the control box opening a second passage fluidly connected to the aspiration lumen,
 a priming valve fluidly connecting the first and second passages when opened, and
 further comprising the step of, prior to the step of inserting the aspiration catheter, operating the priming valve to evacuate air from the pump.

\* \* \* \* \*